United States Patent
Chishti et al.

(10) Patent No.: US 7,037,108 B2
(45) Date of Patent: May 2, 2006

(54) METHODS FOR CORRECTING TOOTH MOVEMENTS MIDCOURSE IN TREATMENT

(75) Inventors: Muhammad Chishti, Sunnyvale, CA (US); Loc X. Phan, Milpitas, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 10/280,535

(22) Filed: Oct. 24, 2002

(65) Prior Publication Data

US 2003/0049584 A1 Mar. 13, 2003

Related U.S. Application Data

(63) Continuation of application No. 10/087,126, filed on Feb. 28, 2002, now Pat. No. 6,499,997, which is a continuation of application No. 09/779,802, filed on Feb. 7, 2001, now Pat. No. 6,394,801, which is a continuation of application No. 09/454,786, filed on Dec. 3, 1999, now Pat. No. 6,227,851.

(60) Provisional application No. 60/110,868, filed on Dec. 4, 1998.

(51) Int. Cl.
    *A61C 3/00* (2006.01)
(52) U.S. Cl. .................................................. 433/24
(58) Field of Classification Search .............. 433/6, 433/24
    See application file for complete search history.

(56) References Cited

U.S. PATENT DOCUMENTS

| 1,831,390 A | 11/1931 | Lindelov |
| 2,851,728 A | 9/1958 | Spalten et al. |
| 3,983,628 A | 10/1976 | Acevedo |
| 4,001,938 A | 1/1977 | Cooper |
| 4,022,419 A | 5/1977 | Haker |
| 4,160,322 A * | 7/1979 | Frazier .................. 433/24 |
| 4,161,065 A | 7/1979 | Gigante |
| 4,671,769 A | 6/1987 | Gill et al. |
| 4,793,803 A | 12/1988 | Martz |
| 4,856,991 A * | 8/1989 | Breads et al. ............ 433/6 |
| 4,983,334 A | 1/1991 | Adell |
| 5,055,039 A * | 10/1991 | Abbatte et al. .......... 433/24 |
| 5,059,118 A * | 10/1991 | Breads et al. ............ 433/6 |
| 5,100,316 A | 3/1992 | Wildman |
| 5,163,840 A * | 11/1992 | Bourke .................. 433/6 |
| 5,186,623 A * | 2/1993 | Breads et al. ............ 433/6 |
| 5,415,542 A * | 5/1995 | Kesling .................. 433/6 |

(Continued)

FOREIGN PATENT DOCUMENTS

EP 0091876 A1 10/1983

(Continued)

OTHER PUBLICATIONS

Nahoum, Henry I., "The vacuum formed dntal contour appliance" New York State Dental Journal (Nov. 1964) 30(9):385-390.

(Continued)

*Primary Examiner*—Todd E. Manahan
(74) *Attorney, Agent, or Firm*—Townsend and Townsend and Crew LLP

(57) ABSTRACT

Appliances are made using a dental mold representing a patient's dental configuration. In particular, thermoformable plastic positioning appliances which fit over the patient's teeth may be formed over a three-dimensional mold of the patient's dentition. An apparatus and methods which employ a manipulable or reconfigurable mold to model patient dentition and gingiva at each stage of treatment. The apparatus and methods are particularly useful for performing midcourse corrections during orthodontic procedures using a plurality of such appliances in sequence.

6 Claims, 9 Drawing Sheets

U.S. PATENT DOCUMENTS

| | | | |
|---|---|---|---|
| 5,795,152 | A | 8/1998 | Glatt |
| 5,876,199 | A * | 3/1999 | Bergersen ..................... 433/6 |
| 5,879,158 | A | 3/1999 | Doyle et al. |
| 5,975,893 | A | 11/1999 | Chisti et al. |
| 6,499,997 | B1 | 12/2002 | Chishti et al. |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 | 12/1998 |
| WO | WO 98/58596 A1 | 12/1998 |

OTHER PUBLICATIONS

Alexander et al., "The DigiGraph Work Station Part 2, Clinical Management," *JCO* (Jul. 1990), pp. 402-407.

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607, 1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty, NATO Symposium on Applications of Human Biostereometrics, Jul. 9-13, 1978," SPIE vol. 166, pp. 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research;* vol. 67, Special Issue Mar. 9-13, 1988, p. 128.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7 , Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, vol. 55, No. 1, (. Jan. 1969),. pp. 23-31.

Crawford, "Computers in Dentistry: Part 1: CAD/CAM: The Computer Moves Chairside," "Part 2: F. Duret—A Man With A Vision," "Part 3: The Computer Gives New Vision-Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models,"

*Plastic and Reconstructive Surgery*, vol. 77, No. 6 (Jun. 1986), p. 877-885.

DCS Dental AG, "The CAD/CAM 'DCS Titan System' for Production of Crowns/Bridges" *DSC Production AG,* Jan. 1992, pp. 1-7.

DeFranco et al., "Three-Dimensional Large Displacement Analysis of Orthodontic Appliances," *J. Biomechanics,* vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al, "CAD-CAM in Dentistry," *Journal of the American Dental Association,* vol. 117 (Nov. 1988), pp. 715-720.

Duret et al., "CAD/CAM Imaging in Dentistry," *Current Opinion in Dentistry,* vol. 1 (1991), pp. 150-154.

Duret, "Vers une prosthese informatisee," (English translation also attached), *Tonus,* vol. 75, (Nov. 15, 1985), pp. 55-57.

Duret, "The Dental CAD/CAM, General Description of the Project," *Hennson International Product Brochure,* Jan. 1986., 18 pages total.

Economides, "The Microcomputer in the Orthodontic Office," *JCO,* (Nov. 1979), pp. 767-772.

Elsasser, "Some Observations on the History and Uses of the Kesling Positioner" *Am. J. Orthod.,* vol. 36, No. 5, (May 1950) pp. 368-374.

Faber et al.,"Computerized interactive orthodontic treatment planning," *Am. J. Orthod.,* vol. 73, No. 1 (Jan. 1978), pp. 36-46.

Felton et al. "A computerized analysis of the shape and stability of mandibular arch form," *Am. Journal of Orthodontics and Dentofacial Orthopedics,* vol. 92, No. 6 (Dec. 1987), pp. 478-483.

Friede et al., "Accuracy of Cephalometric Prediction in Orthognathic Surgery,"Abstract of Papers, *Journal of Dental Research,* vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery,* vol. 48, No. 8, Supp. 1, Aug. 1990, p. 5-6.

Guess et al., "Computer Treatment Estimates in Orthodontics and Orthognathic Surgery, " *JCO,* (Apr., 1989), pp. 262-228.

Heaven et al., "Computer-based Image Analysis of Artificial Root Surface Caries," Abstracts of Papers, *Journal of Dental Research,* vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen,* (Mar. 1991), pp. 375-396.

Huckins, "CAD-CAM Generated Mandibular Model Prototype from MRI Data," *AAOMS* 1999, p. 96.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO,* (Apr. 1988), pp. 478-479.

Jones et al., "An Assessment of the Fit of a Parabolic Curve to Pre- and Post-Treatment Dental Arches," *British Journal of Orthodontics,* vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners Using LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res. ,* vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.,* 32:285-293, 1946.

Kesling, "The Philosophy of the Tooth Positioning Appliance" *Am. J. Orthod. Oral. Surg.,* 31(6):297-304, 1945.

Kleeman et al., "The Speed Positioner" *J. Clin. Orthod.,* 30:673-680, 1996.

Kuroda et al., "Three-Dimensional Dental Cast Analyzing System Using Laser Scanning" *Am. J. Orthod. Dentofac. Orthop.,* 110:365-369, 1996.

Laurendeau et al., "A Computer-Vision Technique for the Acquistion and Processing of 3-D Profiles of Dental Imprints: An Application in Orthodontics," *IEEE Transactions on Medical Imaging,* vol. 10, No. 3 (Sep. 1991), pp. 453-461.

Leinfelder et al., "A new method for generating ceramic restorations: a CAD-CAM system," *Journal Of The American Dental Assoc.,* vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop.* 44, 370-376 (Nr. 5), 1983.

McCann, Inside the ADA, *J. of the Am.. Dent. Assoc.,* vol. 118 (Mar. 1989) pp. 286-294.

McNamara et al., "Invisible Retainers", *J. Clinical Orthodontics,* (Aug. 1985) pp. 570-578.

McNamara et al., Chapter 19: Invisble Retainers, *Orthodontic and Orthopedic Treatment in the Mixed Dentition,* Needham Press, Jan. 1993. pp. 347-353.

Moermann et al., "Computer Machined Adhesive Porcelain Inlays: Margin Adaptation after Fatigue Stress," IADR Abstract 339, *J. of Dent. Research,* vol. 66(a) (1987), p. 763.

Mörmann et al., "Marginal Adaptation von adhasiven Porzellaninlays in vitro,"*Schwizerische Monatsshrift fur Zahnmedizin,* vol. 85 (1985), p. 1118-1129.

Nahoum, "The Vacuum Formed Dental Contour Appliance" *The New York State Dental Journal,* 30(9):385-390, Nov. 1964.

Nash, "CEREC CAD/CAM Inlays: Aesthetics and Durability in a Single Appointment," *Dentistry Today,* (Oct. 1990), pp. 20, 22-23, 54.

Nishiyama et al., "A New Construction of Tooth Repositioner by LTV Vinyl Silicone Rubber" J. Nihon University School of Dentistry, 19(2):93-102, 1977.

Pinkham, "'Foolish' Concept Propels Technology," *Dentist,* Jan./Feb. 1989, 3 pages total.

Pinkham, "Inventor's CAD/CAM may transform dentistry," *Dentist,* Sep. 1990, 3 pages total.

Ponitz,"Invisible Retainers", *Am. J. Orthodontics,* vol. 59, No. 3, Mar. 1971, pp. 266-272.

Procera Research Projects, *PROCERA Research Projects 1993—Abstract Collection*, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58, No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing finishing problems with the mini-positioner" *Am. J. Orthod.* 59:596-599, 1971.

Siemens, "CEREC—Computer-Reconstruction,"High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed on Jun. 20, 1997, 41 pages total.

Van der Linden et al., "Three-Dimensional Analysis of Dental Casts by Means of the Optocom," *J Dent Res*, Jul.-Aug. 1972, vol. 51, No. 4, p. 1101.

Van der Linden, "A New Method to Determine Tooth Positions and Dental Arch Dimensions," Jul.-Aug. 1972, p. 1104.

Van der Zel, "Ceramic-fused-to-metal Restorations with a New CAD/CAM System," *Quintessence International*, vol. 24(11) (1993), pp. 769-778.

Várady et al., Reverse engineering of geometric models—an introduction. Computer-Aided Design, 29 (4):255-268; 1997.

Warunek et al., "Clinical use of silicone elastomer appliances" *JCO*, MH (10):694-700, 1989.

Warunek et al., "Physical And Mechanical Properties of Elastomers in Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution,"*Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis Of Three-Dimensional Tooth Movement in Orthodontics," *Frontiers in Med. and Biol. Eng'g*, vol. 1, No. 2 (1988), pp. 119-130.

* cited by examiner

METHODS FOR CORRECTING TOOTH MOVEMENTS MIDCOURSE IN TREATMENT

CROSS-REFERENCES TO RELATED APPLICATIONS

This application is a continuation of application Ser. No. 10/087,126 filed Feb. 28, 2002, now U.S Pat. No. 6,499,997 which was a continuation of application Ser. No. 09/779,802, filed Feb. 7, 2001, now U.S. Pat. No. 6,394,801 which was a continuation of application Ser. No. 09/454,786, filed Dec. 3, 1999, now U.S. Pat. No. 6,227,851, which claimed the benefit and priority of U.S. Provisional Patent Application No. 60/110,868, filed Dec. 4, 1998, the full disclosures of which are hereby incorporated by reference for all purposes.

BACKGROUND OF THE INVENTION

The present invention is related generally to the field of orthodontics. More particularly, the present invention is related to a dental model system which can be manipulated to model a series of tooth configurations for a single patient throughout orthodontic treatment.

Orthodontic treatments involve repositioning misaligned teeth and improving bite configurations for improved cosmetic appearance and dental function. Repositioning is accomplished by applying gentle controlled forces to the teeth over an extended period of time. Due to the limited space within the oral cavity and extensive movements that some teeth must undergo, the teeth will often be moved throughout a series of intermediate patterns to properly arrange the teeth. For example, molars may be temporarily distalized to create adequate space for movement of the incisors. Thus, a single patient may experience an average of 25–30 stages or alignment patterns before achieving the final desired configuration.

Such repositioning may be accomplished with a variety of orthodontic treatments and dental appliances, including conventional braces, spring retainers, positioners, and other removable aligners. With any treatment, an initial mold of the patient's teeth is made. This mold provides a model of the patient's teeth that the orthodontist uses to formulate a treatment strategy. In some instances, it may be desirable to create additional molds of the patient's teeth throughout the treatment plan to reflect individual stages. For example, the treatment strategy may be re-evaluated or a dental appliance may need to be fit to an intermediate tooth configuration.

The need for intermediate tooth configuration molds is particularly significant when using removable elastic appliances to move the teeth. Such elastic appliances typically include a thin shell of elastic material that generally conforms to the pattern of a patient's teeth, but is slightly out of alignment with the initial tooth configuration. By properly choosing the alternate configuration, placement of the elastic appliance over the teeth will move individual teeth to a desired position. Over time, multiple elastic appliances used in successive stages of treatment, will move the teeth to intermediate or final tooth positions. Such a system is described in U.S. Pat. No. 5,975,893, and in published PCT application WO 98/58596 which designates the United States and which is assigned to the assignee of the present application. Both these documents are incorporated by reference for all purposes. When using elastic appliances as described above, a series of appliances are made to reflect the successive stages of treatment. Such appliances are typically made by heating and vacuum or pressure-sealing a sheet of thermoformable plastic over the dentition of a mold.

Traditional methods of dental mold making may be utilized to fabricate a mold for such use. These methods require first forming an impression of the patent's dentition using a suitable impression material, such as alginate or polyvinylsiloxane (PVS). Plaster is then poured into the impression to create a permanent, three-dimensional mold of the dentition. To create an appliance to reflect the next desired tooth configuration in the series of treatment stages, a new mold must be created to reflect the desired configuration. This involves individually cutting the teeth from the mold and resetting the teeth in the desired configuration. Wax is then used to fill in the spaces and represent gingiva. This is a tedious process which compounds both cost and time of treatment for the patient. Resetting is accomplished by either taking into service a laboratory technician or by sending the mold out to a dental laboratory. This process typically requires 2.5 weeks to be accomplished. This represents lost time in the treatment plan as the patient cannot progress to the next stage of treatment until a positioning appliance with the new desired configuration is created. Since such an orthodontic treatment may require, for example, 25 intermediate reset molds to represent 25 stages of treatment progress, the cost and time required for such mold making may be prohibitively high.

The process of iterative mold making may be improved with the use of digital imaging and computer controlled molding systems. Here the patient's initial tooth arrangement and shape of the patient's dental arch are represented by a digital data set. The data set can then be manipulated to reflect progressive tooth arrangements. For each arrangement, the data may be used to guide computerized model fabrication systems to create a corresponding three-dimensional mold. Such techniques may speed production time and reduce costs by eliminating the need for artistic resetting of teeth in mold manufacturing.

Although the above described process aids in the production of iterative molds, further improvement may be desired. The cost in time and materials to produce each mold, though lessened, may still be significant. This cost is additive, as each new stage in treatment or each change in treatment requires the production of a new mold. Likewise, the cost of storing a series of molds for each patient throughout treatment may be formidable. In addition, it may be desirable to visualize a sequence of treatment stages, particularly in an academic environment or in a preliminary patient meeting.

For these reasons, it would be desirable to provide an alternative apparatus and methodology for realizing a series tooth configurations. Such apparatus and methods should be economical, reusable, reduce time consumption, reduce material waste, and, in particular, should reduce the need for fabricating multiple casts of teeth arrangements for stages in the orthodontic treatment. At least some of these objectives, as well as others, are met by the apparatus and methods of the invention described hereinafter.

BRIEF SUMMARY OF THE INVENTION

An improved method for repositioning teeth is provided using appliances, typically comprising polymeric shells, having cavities shaped to receive and resiliently reposition teeth. The improvement includes determining at the outset of treatment, a geometry for at least one appliance selected to move the teeth to a desired intermediate arrangement and at a later time (usually after the teeth have been moved through at least one, and usually at least two, three, four, five, or more stages) determining one or more geometries for at least one additional appliance having a geometry selected to move the teeth from an actual intermediate arrangement to a successive intermediate or final tooth arrangement. The actual intermediate tooth arrangement may be determined by any available method, usually by taking a mold and optically scanning the mold, but optionally by direct optical or other scanning of the patient's teeth.

DETAILED DESCRIPTION OF THE INVENTION

The present invention provides an apparatus and methods to produce and operate a manipulable dental model system to model a series of tooth and gingiva configurations for a single patient throughout orthodontic treatment. The tooth and gingiva configurations represent each stage of treatment from initial presentation, through intermediate stages and to the final desired configuration. The manipulable model system may be used for a variety of purposes, particularly for the production of polymeric and other elastic positioning appliances.

Figure 1:
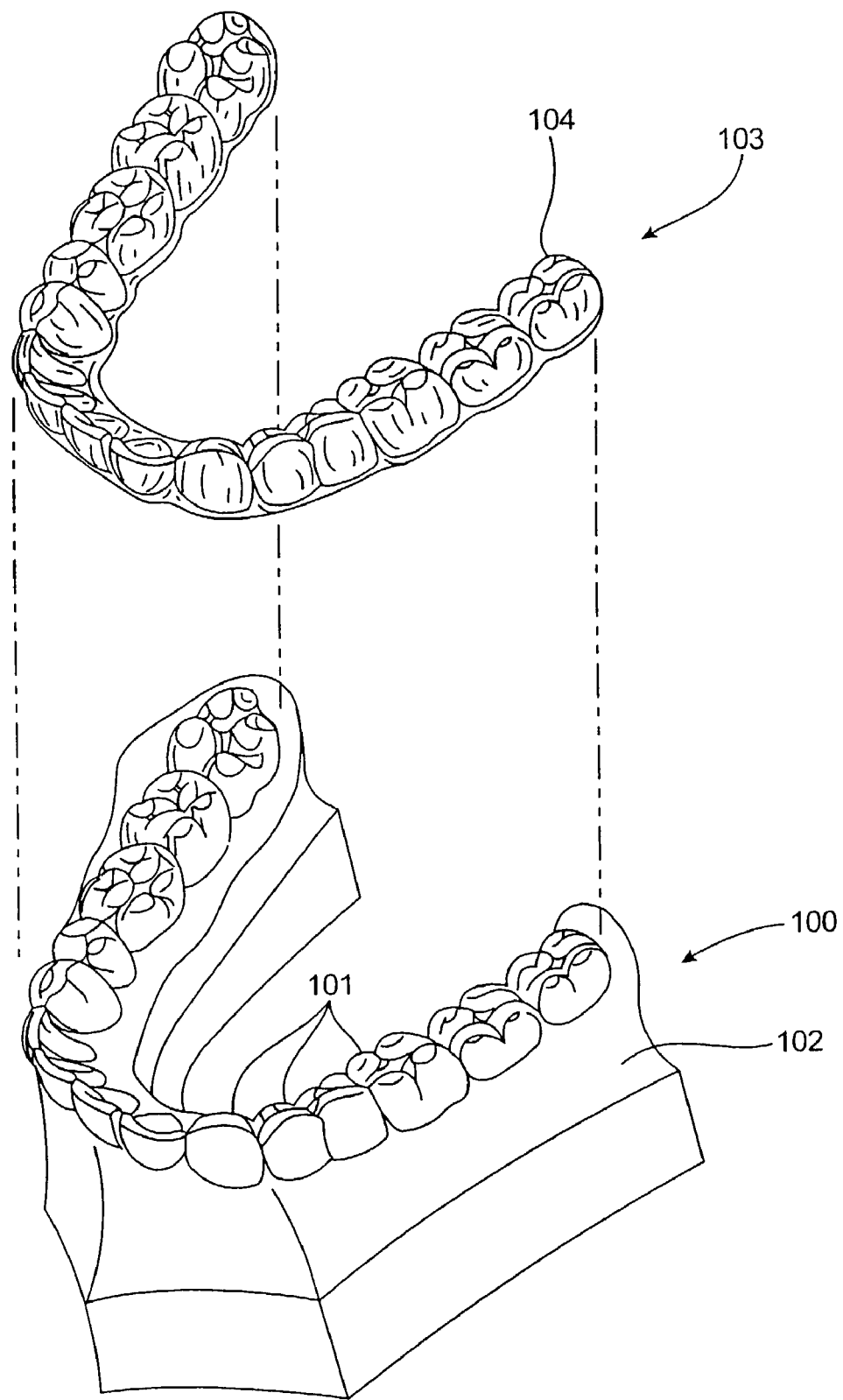
FIG. 1 is a simplified illustration of a reconfigurable dental model system and an elastic positioning appliance fabricated with its use.

In one embodiment of the present invention, a single dental model system is manipulated and reconfigured to model different tooth configurations by controlling the movement of at least some of the individual tooth members, or groups of members, with manipulation mechanisms. Referring to FIG. 1, a simplified illustration of such a manipulable dental mold 100 for the fabrication of dental appliances is shown. In this illustration, the mold 100 is a positive representation of the tooth configuration and dental arch of the lower jaw. The tooth configuration is created by the placement and alignment of tooth members 101. The individual tooth members 101 are typically produced to resemble the individual shape of each of the patient's natural teeth. Although not shown, this may also include any type of dental feature, including but not limited to fillings, caps, crowns, dentures, implants, grafts, and dental appliances. In a preferred embodiment, the tooth members 101 are inserted into ports (not shown) in the frame 102 to support the configuration. It is through these ports that the tooth members may be manipulated.

Also shown in FIG. 1 is a an exemplary dental appliance, specifically an elastic positioning appliance 103, which may be produced with use of the mold 100. The appliance 103 comprises a polymeric shell 104 having an inner cavity (not shown) on the underside of the shell 104 which is shaped to receive and resiliently reposition teeth from one tooth arrangement to a successive tooth arrangement. The appliance 103 is preferably formed from a thin sheet of a suitable elastomeric polymer, such as Tru-Tain 0.03 in. thermal forming dental material (Tru-Tain Plastics, Rochester, Minn.), or Essix A-Type or Essix B-Type thermal forming material (Raintree-Essix, New Orleans, La.). The overall method for producing incremental position adjustment is provided in U.S. Pat. No. 5,975,893, previously incorporated by reference. But, in general, the shell 104 is typically produced by heating a thermoformable polymer sheet and vacuum or pressure forming the sheet over the tooth members 101 of the mold 100. Thus, the shell 104 is a direct representation of the characteristics of the mold 100. If this appliance 103 is worn by a patient as a stage in orthodontic repositioning, the shell 104 will preferably, but not necessarily, fit over all teeth or dental features supported by the patient's dental arch. Those teeth which are to be repositioned will be slightly misfit by the appliance to allow force and movement into the desired positions.

Figure 2:
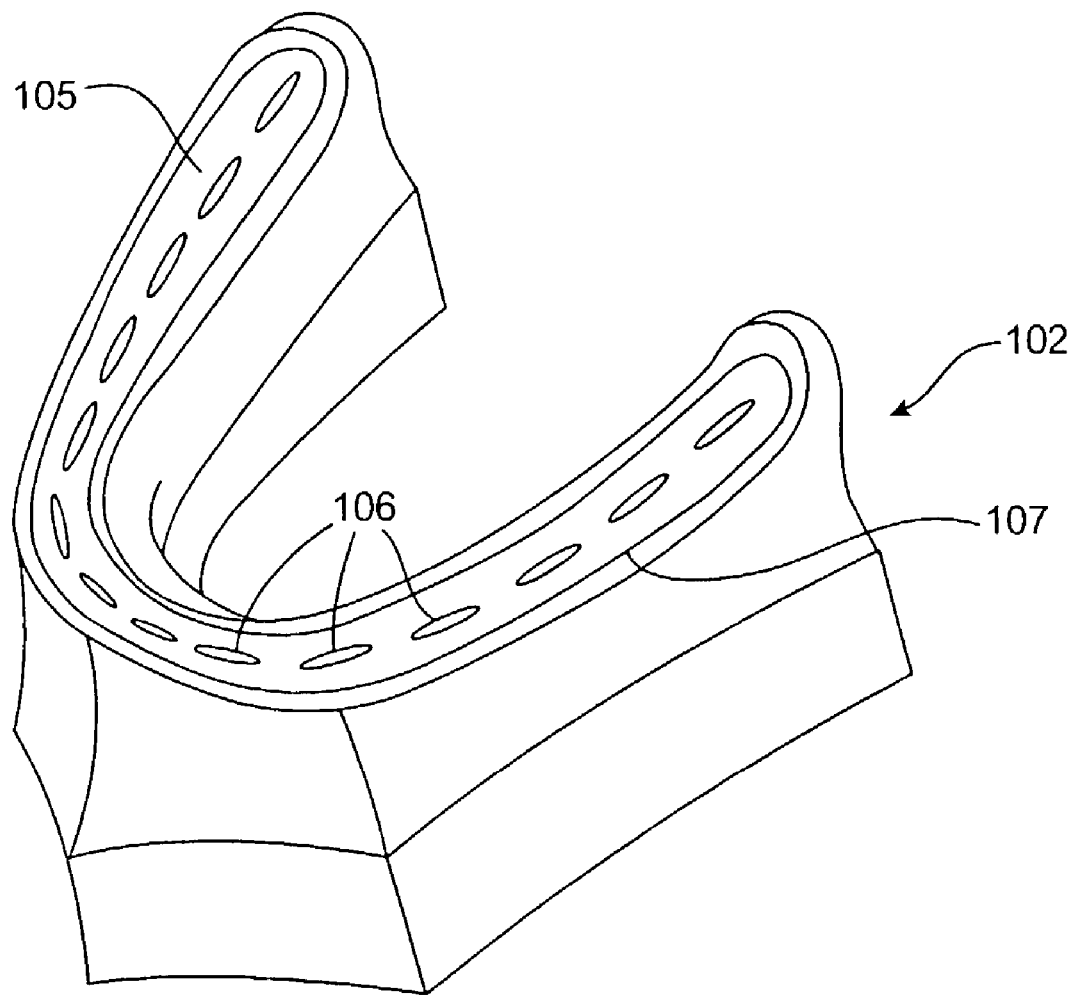
FIG. 2 is a perspective view of an embodiment of the frame of the present invention.

As described, the tooth members 101 are supported by a frame 102, which houses the manipulation mechanisms. A preferred embodiment of the frame 102 is depicted in FIG. 2. The frame 102 is designed to have a hollow interior portion 105 and may include a plurality of ports 106 positioned horizontally along the gingival line 107 at locations which allow for placement of the tooth members 101. The positioning of the ports 106 is meant to correspond generally to the patient's actual or desired tooth positions. The ports 106 are sized such that adequate space is available to avoid interference with the movement of the tooth members 101. Thus, the ports 106 may be oblong or elliptical, as shown, or they may form a variety of shapes, including rectangular, circular, multi-sided and/or multi-curved. Likewise, the ports 106 maybe replaced by a continuous channel or track, or the interior portion 105 may not be present, obviating the need for ports.

Figure 3:
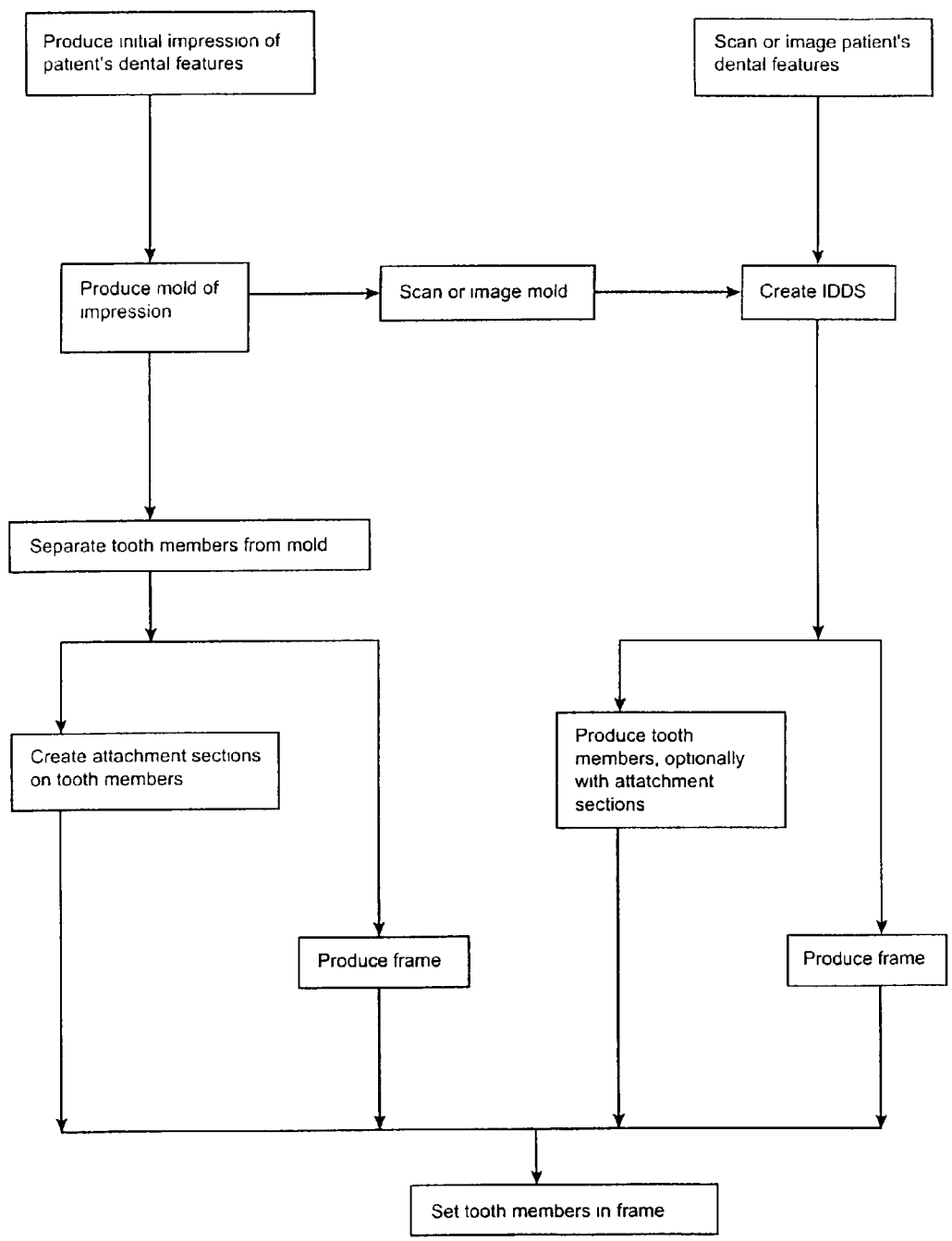
FIG. 3 is a flow diagram of production options for the dental model system.

The tooth members 101 and frame 102 of the dental model system may be produced manually or with the use of digital imaging and computer controlled molding systems, as described previously. These production options are presented in a flowchart, FIG. 3. Regardless of the production methodology, the resulting components may then be assembled.

Figure 4:
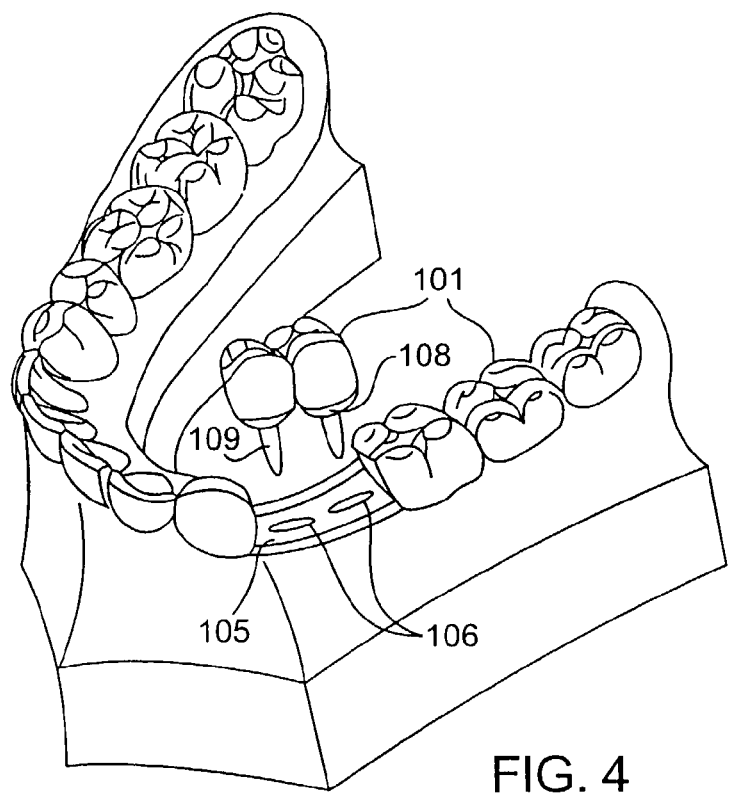
FIG. 4 illustrates an embodiment of arranging the tooth members in the frame by inserting the coupling members through the ports.
Figure 5:
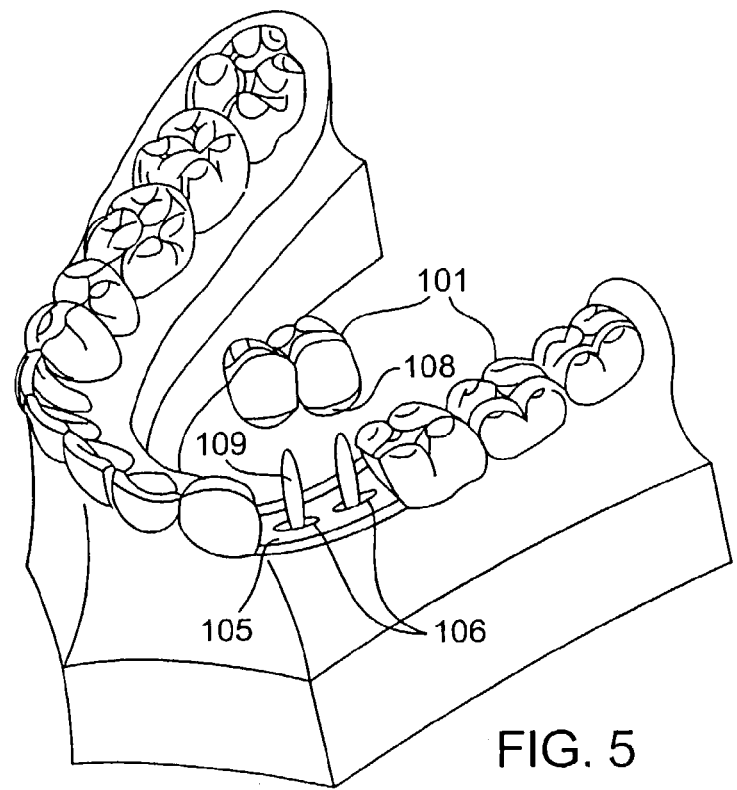
FIG. 5 illustrates an embodiment of arranging the tooth members in the frame by placing the tooth members on coupling members protruding through the ports.

The tooth members 101 may be coupled to one or more manipulation devices by any of a variety of means. Referring to FIG. 4, an attachment sections 108 may be present on a bottom portion of the tooth members 101. The attachment sections 108 may be connected to coupling members 109 which may be inserted through the ports 106 for coupling to a manipulation mechanism. Alternatively, referring to FIG. 5, the coupling member 109 may be integral with the manipulation mechanism. In this case, the coupling members 109 may appear as posts or shafts protruding through the ports 106. The tooth members 101 may then be coupled to the coupling member 109 by means of an attachment section 108.

Figure 6:
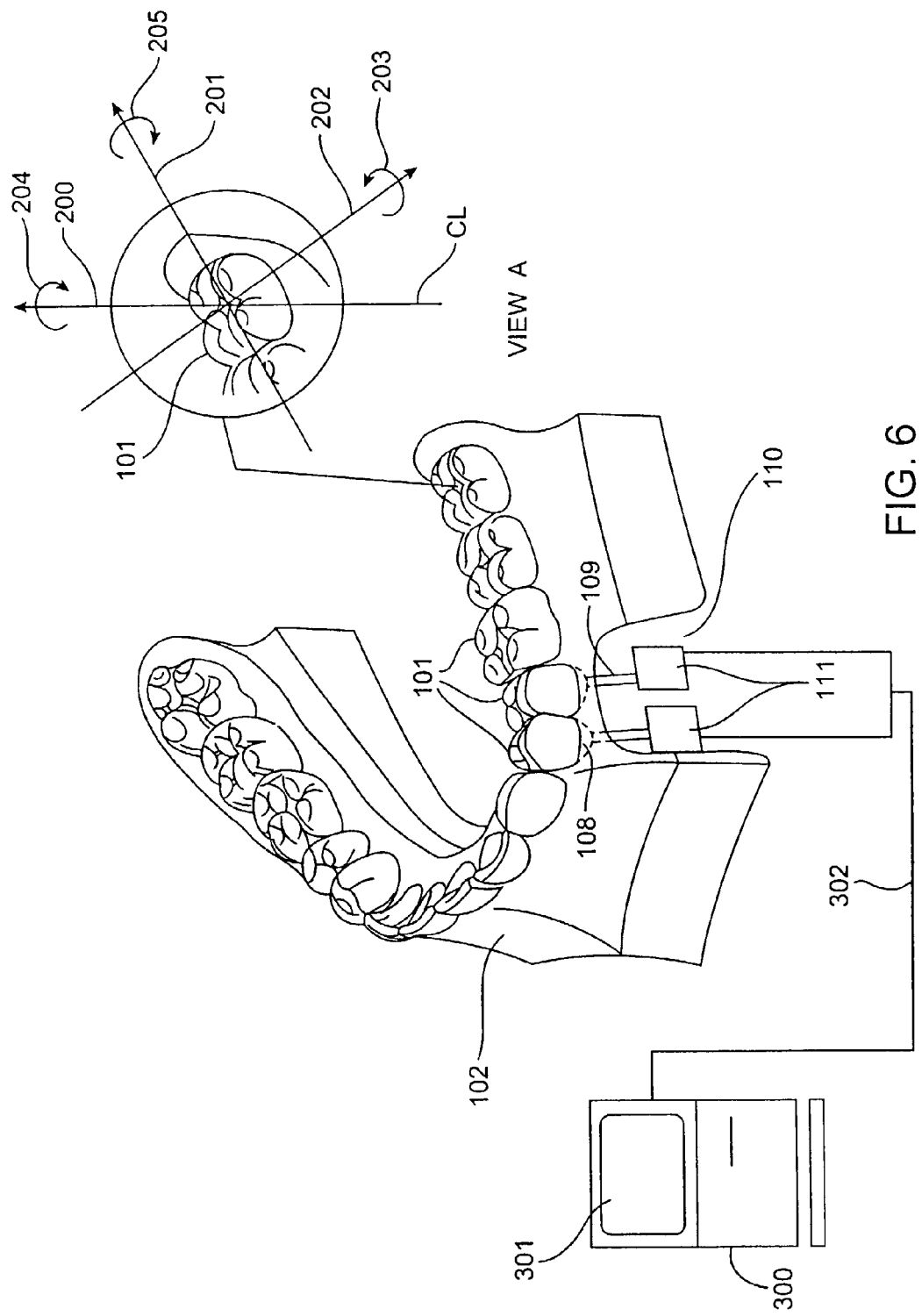
FIG. 6 is a simplified cut-away perspective view of the dental model system, revealing an embodiment of the manipulation devices, including View A which illustrates possible degrees of freedom in movement of each tooth member.

In a preferred embodiment, the ports 106 provide access to the inner portion 110 of frame 102, as shown in FIG. 6. The inner portion 110 houses one or more manipulation devices 111 which manipulate the tooth members 101. Once coupled to the manipulation devices 111, the tooth members 101 can be actuated and repositioned. The manipulation devices 111 are described in more detail below.

The simplified cut-away view of dental mold 100 shown in FIG. 6, reveals manipulation devices 111 disposed in the interior portion 110 of the frame 102. The manipulation device 111 can be a single mechanism, linked simultaneously to each individual tooth member 101 or group of members using, for example, a series of mechanical linkages or other similar means. However, as shown in FIG. 6, each tooth member 101 is preferably individually linked and controlled by a single manipulation device 111. Optionally, the tooth members 101 can be actuated by a combination of manipulation devices each providing some degree of manipulation within a given coordinate system.

To understand how tooth members 101 may be moved by a manipulation device 111, an arbitrary centerline CL is drawn through one of the tooth members 101, as seen in View A of FIG. 6. With reference to centerline CL, the tooth members 101 may be moved in the orthogonal directions represented by axes 200, 201, and 202 (where 200 is the centerline). A tooth member 101 may be translated along axes 201 and 202, or along any vector in the plane defined by these axes. Likewise, a tooth member 101 may be extruded or intruded by movement along axes 200. Torquing may be accomplished by rotation around axes 200, as represented by arrow 204. Rotation may also occur in the opposite direction than as indicated by arrow 204. Tipping or angulation may be achieved by rotation around axes 201 and 202, as represented by arrows 205 and 203 respectively. Similarly, rotation may also occur in the opposite direction than as indicated by these arrows. Thus, it is possible to perform movement of each tooth member 101 in six degrees of freedom (six DOF).

Accordingly, a practitioner can individually manipulate and arrange the tooth members 101 on the mold 100 to replicate a predetermined tooth arrangement. Each arrangement of the tooth members 101 may correspond to an incremental change in the configuration of the patient's teeth to provide a prescribed tooth movement required in each stage of an orthodontic treatment step.

The performance of six DOF movement usually requires a combination of components working individually and/or in unison to complete the various desired movements. In one exemplary embodiment, a tooth member 101 is coupled to a coupling member 109 at attachment section 108 at the bottom portion of the tooth member 101. Coupling member 109 is shown simplistically in FIG. 6 as a single member for illustrative purposes only. Since the coupling member 109 may need to provide multiple degrees of motion to tooth member 101, it may include many forms, shapes, and/or sizes. For example, certain movements may require that the coupling member 109 include one or a series of mechanical linkages, gears, springs, levers, hinges, cams, magnets and/ or pneumatic pistons, used alone or in combination. The coupling member 109 couples the tooth member 101 to the manipulation device 111, also shown in a simplistic fashion merely for illustrative purposes and for generally understanding of placement.

Like the coupling member 109, the manipulation device 111 can be any single or combination of mechanical or electromechanical components that can be used to translate a driving force (electric or mechanical) into the directional movement of a member. For example, the manipulation device 111 may include a series of gears coupled to coupling member 109 and driven by a stepper motor. The motor receives a driving force, optionally from an external source, to drive the gears and incrementally rotate (i.e. arrows 203, 204, or 205) the coupling member 109, such that a degree of rotational movement is created in tooth member 101. Although, the actual mechanism used to provide the articulation of the tooth member 101 may comprise any number of interlinked components, it is likely that some of the components for providing such motion will be taken from the group comprising for example mechanical linkages, gears, springs, levers, hinges, cams, magnets and/or pneumatic pistons, used alone or in combination, as well as servos, solenoids, motors, electronics, solid state components, and the like. Alternatively, manipulation device 111 can be directly coupled to tooth member 101 without using intervening coupling member 109.

The manipulation devices 111, which create the actual six DOF movement of the tooth members 101, may be controlled manually and/or with the use of a microprocessor. In one embodiment, the repositioning of the individual tooth members 101 involves at least some of the components of manipulation device 111 being manually operated (non-computer aided). The manual controls may include, but are not limited to, knobs, screws, switches, joysticks, and other similar manual control mechanisms. In this embodiment, the practitioner will manually actuate each control mechanism, usually with finger pressure, which will in turn actuate the inner components of the manipulation device until a desired tooth arrangement is produced. Likewise, manual operation may be assisted with the visual aide of computer graphics or with instructions provided by software code.

In a preferred embodiment, the apparatus and methods of the present invention rely on the manipulation of manipulation devices 111 using a computer 300 or a workstation having a suitable graphical user interface (GUI) 301. In a specific example shown in FIG. 6, computer 300 is electrically coupled to manipulation device 111 to enable computer generated instructions to be sent to manipulation devices 111 via appropriate and well-known computer coupling methods, represented as line 302. The manipulation of tooth members 101 is driven using software appropriate for viewing and modifying the images (see above) on the GUI 301, as well as directing and controlling the tooth movements. Specific aspects of the controlling/directing software is described in detail hereinafter.

Figure 7:
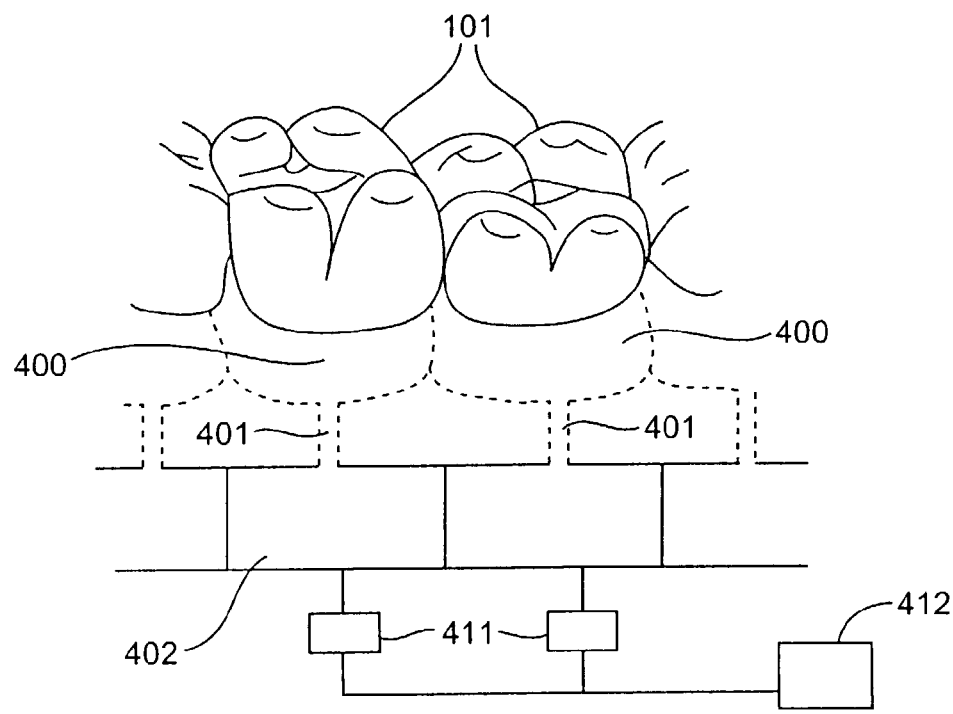
FIG. 7 illustrates an embodiment of manipulable simulated gingiva involving inflatable bladders.
Figure 8:
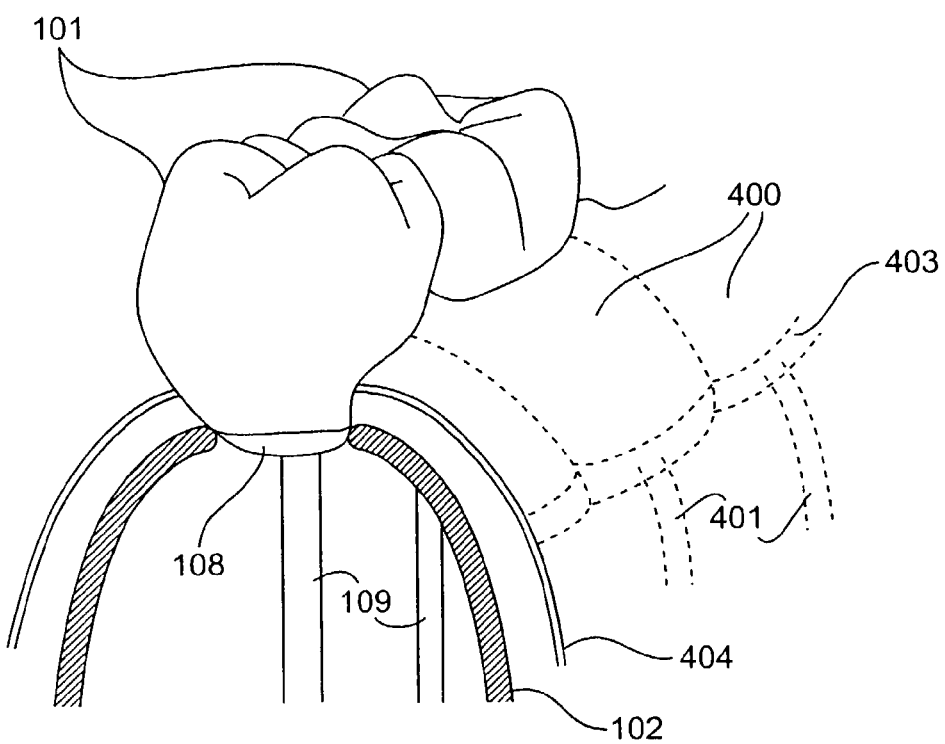
FIG. 8 is a cut-away perspective view of an embodiment of the inflatable bladders in relation to the tooth members and frame of the dental model system.
Figure 9:
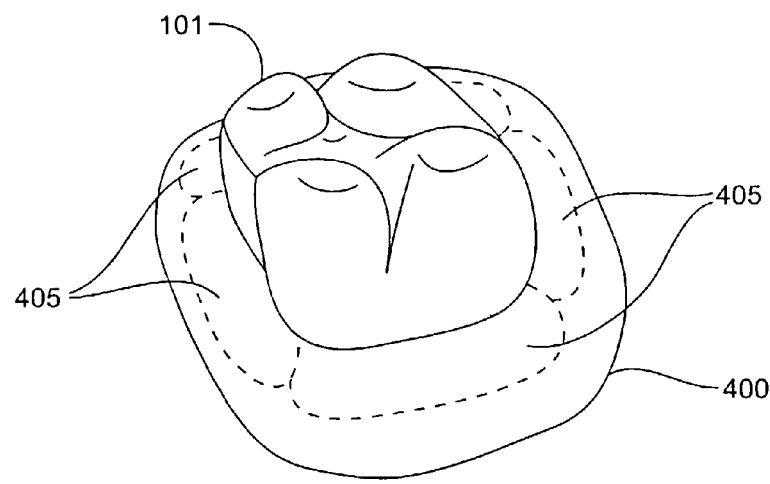
FIG. 9 illustrates an embodiment of sub-bladders within an inflatable bladder.

In a preferred embodiment of the present invention, the dental model system may be comprised of independently reconfigurable gingiva, in addition to tooth members, to model different tooth configurations with supporting simulated gingiva. One embodiment of reconfigurable simulated gingiva is schematically represented in FIGS. 7–9. Here, a series of inflatable bladders 400 surround each tooth member 101. As shown in FIG. 7, at least one bladder 400 is typically present to simulate the gingiva surrounding each tooth member 101. However, not depicted, each bladder 400 may simulate the gingiva surrounding more than one tooth member 101, or one continuous bladder 400 may simulate the gingiva surrounding all tooth members 101. The bladders 400 are comprised of an elastomeric material filled with air, liquid or a suitable medium. Each bladder 400 may have its own inflation port 401, leading to its own source 402. Therefore, each bladder 400 may be independently inflated and deflated by actuation of a control mechanism 411. Alternatively, the inflation ports 401 may be partially or wholly interconnected allowing manipulation of the bladders 401 with a reduced number or sources 402 or control mechanisms 411. Actuation of the control mechanism 411 may be manual or controlled by a digital processor 412.

Referring to FIG. 8, a simplified cut-away perspective view of the manipulable dental model system, reveals the possible placement of the inflatable bladders 400. The boundaries of the bladders 400 are represented by dashed lines 403. The bladders 400 may be located on the outside wall of the frame 102, which houses the attachment sections 108 and coupling members 109 which are linked to the tooth manipulation devices (not shown). Typically, the bladders 400 are covered by a continuous sheet 404 of elastomeric material to provide a smooth, consistent surface. However, the bladders 400 may alternatively be present without a cover.

Manipulation of the simulated gingiva may be further refined by a number of design features. First; each inflation bladder 400 may house a number of smaller sub-bladders 405, as shown in FIG. 9. The sub-bladders 405 may be inflated with air, liquid or a suitable medium which may or may not be the same as that which fills the main inflation bladder 400. Likewise, the sub-bladders 405 may be comprised of a material which may or may not be the same as the main inflation bladder 400. Differences in material and inflation medium may provide differing inflation dynamics. Second, each inflation bladder 400 may be comprised of a variable wall to provide differing inflation dynamics throughout the bladder 400. The wall may vary in thickness, material, amount of crosslinking of the material and number of layers, to name a few. Each variant may provide a different dynamic. For example, a portion of a bladder comprised of thin wall material will distend at a quicker rate than a portion of the bladder comprised of a thicker wall material. Thus, the simulated gingiva may be manipulated to replicate fine details of the patient's gingival configuration.

Figure 10:
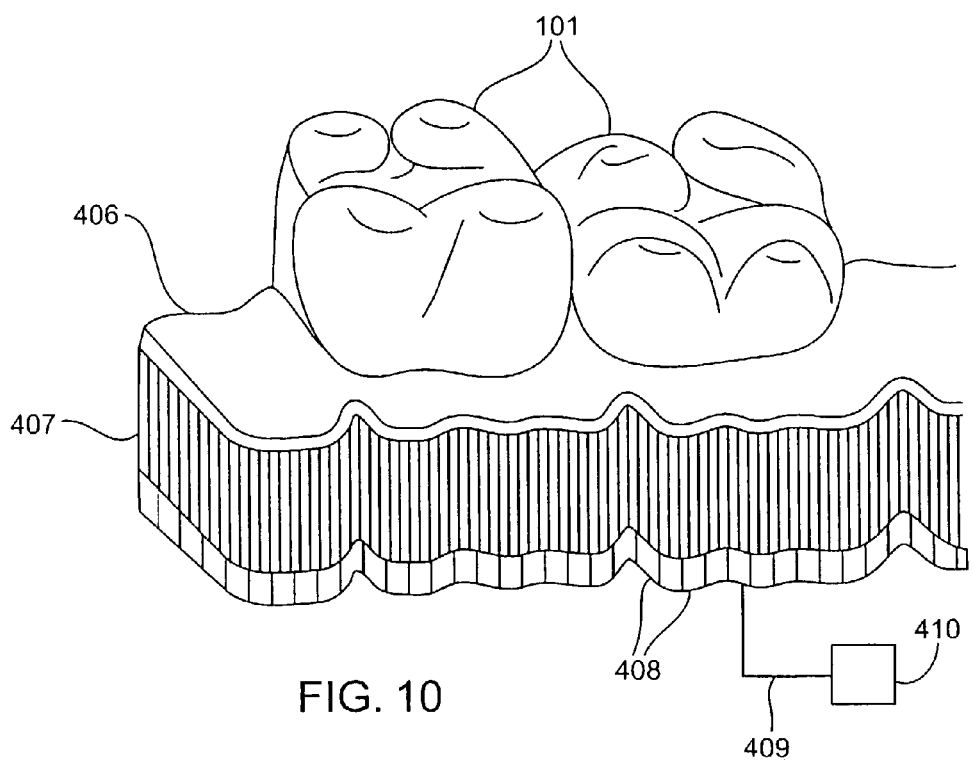
FIG. 10 is a perspective view of an embodiment of manipulable simulated gingiva involving movable support shafts.

Another embodiment of reconfigurable simulated gingiva is schematically represented in FIG. 10. Here, the simulated gingiva may be comprised of a flexible sheeting 406 of any suitable material, such as nylon, silicone, latex rubber, polyurethane, woven materials or cloth. Attached to the underside of the sheeting 406 may be a series of support shafts 407. The support shafts 407 may be of any cross-sectional geometry and dimension. The support shafts 407 may be manipulated individually or in groups by control mechanisms 408, similar in concept to the manipulation devices 111 used to manipulate the tooth members 101. Like the tooth members 101, the support shafts 407 may be manipulated in up to six degrees of freedom and the control mechanisms 408 may be electrically coupled 409 to a digital processor 410 for processor control.

Figure 11:
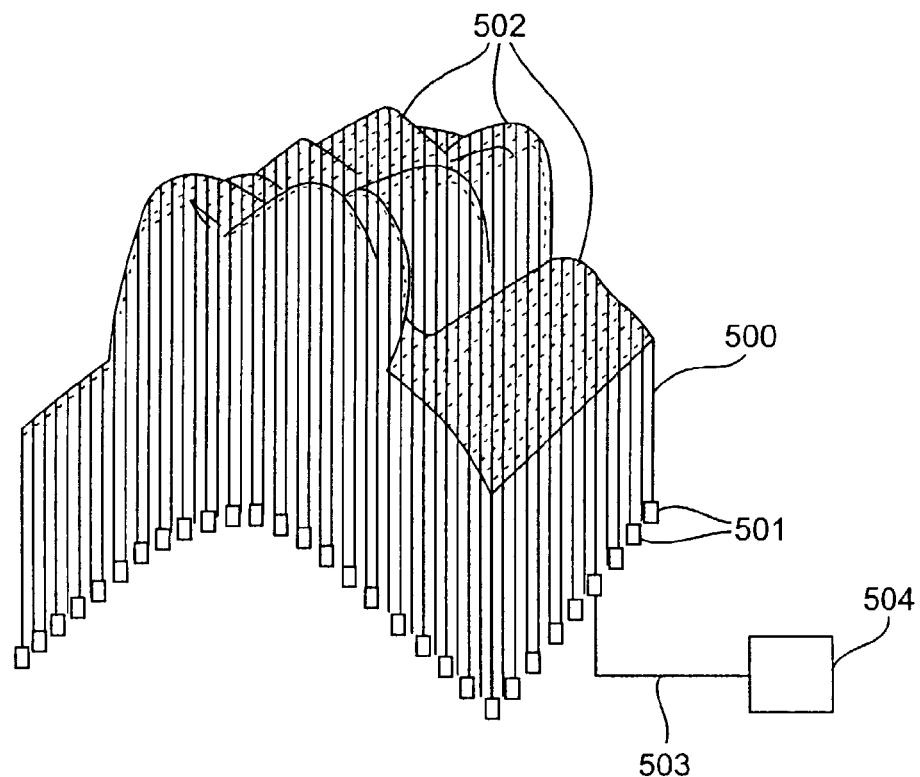
FIG. 11 is a perspective view of an embodiment of a reconfigurable dental model system comprised of movable model shafts.

Additional embodiments of the present invention involve alternative designs and methods of reconfiguring a single dental model system to model different tooth and gingiva configurations. Referring to FIG. 11, a single model system may be comprised or partially comprised of a series of model shafts 500. The model shafts 500 may be of any cross-sectional geometry and dimension, and they may have any tip design. The model shafts 500 may be manipulated individually or in groups in the vertical direction by one or more control mechanisms 501, represented by boxes. Upon actuation of the mechanisms 501, the model shafts 500 may be raised to varying levels. Together, the tips 502 of the shafts 500 may form the surface features of the tooth members, gingiva and other dental features. New configurations may be created by simply altering the tip levels by manipulating the model shafts 500. The model shafts 500 may be manipulated manually by the control mechanisms 501. alternatively, the control mechanisms 408 may be electrically coupled 503 to a digital processor 504 for processor control.

Figure 12A:
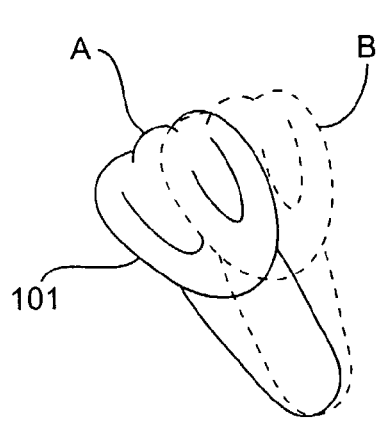
FIGS. 12A and 12B illustrate an embodiment of a method of reconfiguring a dental model system involving resurfacing.
Figure 12B:
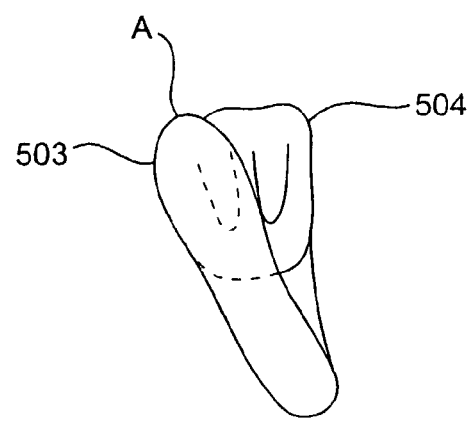

Referring now to FIGS. 12A and 12B, a single model system may be reconfigured to model different tooth and gingiva configurations by repeated resurfacing of the original mold. For example, as shown in FIG. 12A, it may be desirable to angulate a tooth member 101 from position A, represented by a solid line, to position B, represented by a dashed line, in the original mold. Rather than separating, angulating and recoupling the tooth member 101 to the mold, the tooth member 101 may remain in position A and be resurfaced. As shown in FIG. 12B, portions of the tooth member 101 may be removed, leaving a core 503, represented in black, in position A. A new material portion 504, represented in white, may be added to the right side to create the appearance that the tooth member 101 has moved to position B. Such resurfacing may be repeated to create different tooth and gingival configurations.

When using the reconfigurable dental mold 100 to produce a series of elastic positioning appliances 103 for orthodontic treatment, the mold 100 may be manipulated through a series of tooth configurations representing each stage in orthodontic treatment. As described previously, the initial tooth configuration is represented by the IDDS. This digital information is introduced to computer 300 for manipulation of the mold 100. The IDDS data serves as a baseline from which manipulation of the tooth members 101 begins. The Align Technology software (TREAT) described above, may be employed to determine the final tooth arrangement prescribed as the goal of the orthodontic treatment. Alternatively, the teeth may be virtually repositioned based on the visual appearance or instruction from the orthodontist. However, once the user is satisfied with the final arrangement of teeth, the final tooth arrangement is incorporated into a final digital data set (FDDS). Based on both the IDDS, FDDS, and optionally user input, a plurality of intermediate digital data sets (INTDDS's) are generated to correspond to successive intermediate tooth arrangements. The data sets are then reviewed by the orthodontist for accuracy.

In a preferred approach, the practitioner may direct the software to send an instruction to a manipulation device 111 to direct a tooth member 101 to move to a position which corresponds to a position digitally represented in the INTDDS and/or FDDS and visually represented on GUI 301. After the tooth members 101 are each manipulated and arranged to correspond to the INTDDS and/or to the FDDS data, the dental model system can be used to fabricate the system of incremental elastic positioning appliances 103 as described below.

Figure 13:
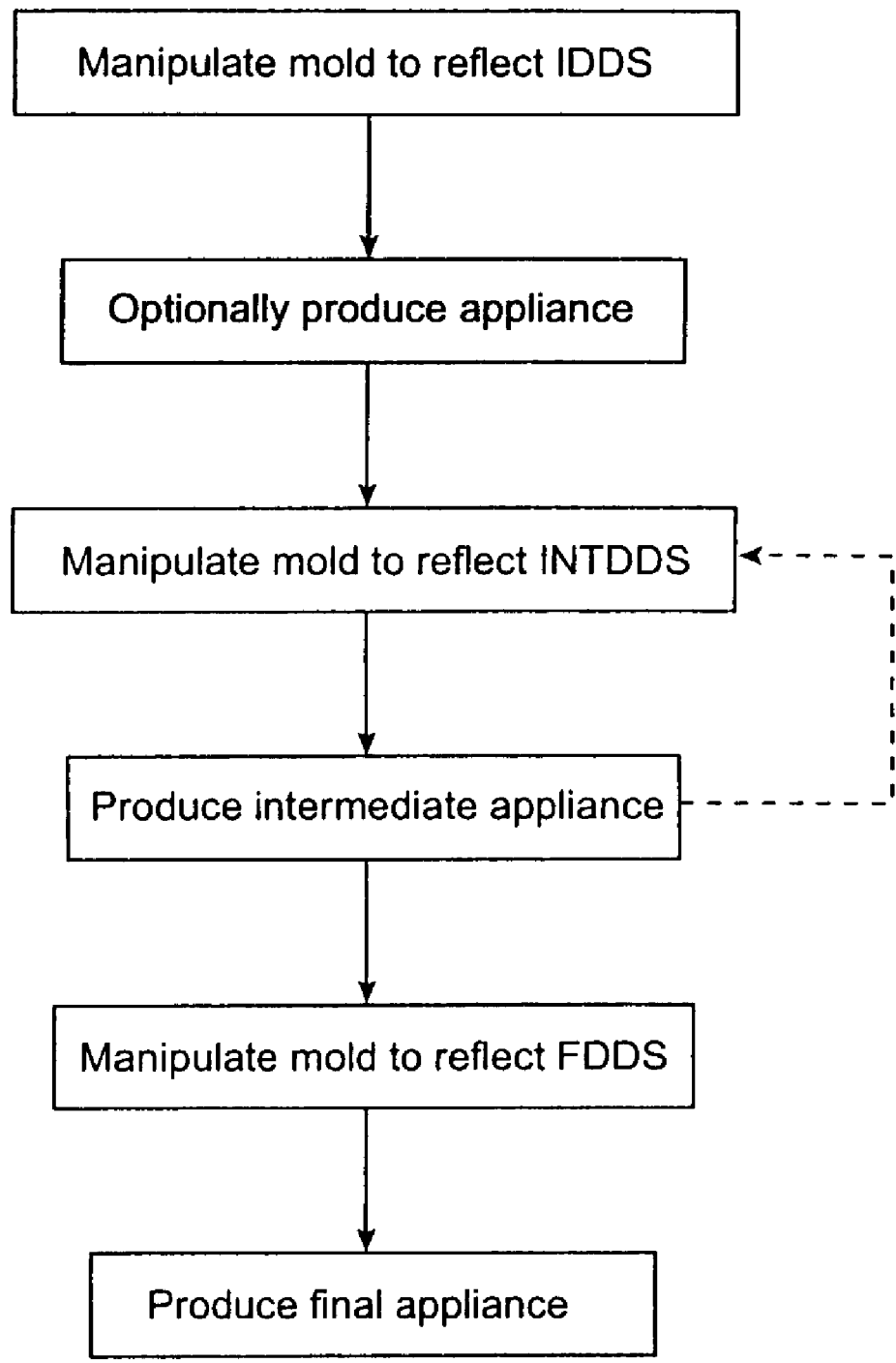
FIG. 13 is a flow diagram of a possible patient treatment method according to the principles of the present invention.

Referring now to FIG. 13, a flow diagram is shown describing an embodiment of a patient treatment method using a manipulable dental mold 100 and elastic positioning appliances 103 according to the principles of the present invention. At the outset of the orthodontic treatment method, the reconfigurable dental mold 100 is manipulated to reflect the initial tooth and gingiva arrangement described by the first digital data set (IDDS). An elastic positioning appliance or other appliances may be produced from the mold in this configuration. The mold 100 may then be manipulated to reflect the first intermediate tooth arrangement prescribed by the first intermediate digital data set (INTDDS). At this point, an elastic positioning appliance may be produced from the manipulable mold for the first stage of treatment in the progressive alignment series. Typically, such treatment involves a series of treatment stages. For each stage, the mold is manipulated to reflect the desired intermediate tooth configuration and a positioning appliance is produced. This is repeated for each INTDDS. Finally, the mold is manipulated to reflect the final tooth configuration prescribed by the final digital data set (FDDS), from which the final positioning appliance is produced. This appliance may be worn until the patient's dental features are properly aligned in the desired final arrangement, and it may be optionally worn thereafter to retain the teeth in the desired position.

The practitioner may choose to create configurations for a sufficient number of appliances at the outset of treatment which can provide the desired treatment goals (i.e. a final tooth arrangement), thus producing an initial set of appliances. For example, the practitioner may determine configurations at the outset for at least three appliances, but most likely more. Preferably the determination of the number of configurations and appliances created is dictated by the number of stages of treatment deemed necessary by the practitioner.

However, not all configurations and appliances need to be determined at the outset of treatment. A practitioner may choose to create from one to all appliances at the outset of treatment or the practitioner may wait and produce some appliances at a later time. Furthermore, it may be necessary to make appliances again at a later time to revise a configuration to redirect the treatment. To this end, the practitioner observes the patient at each stage of the treatment, to determine if a new configuration and appliance or set of configurations and appliances are needed to re-direct the treatment to reach the final tooth arrangement. If at any time after making an observation the practitioner determines that an appliance or set of appliances are not producing the desired intermediate tooth configuration, the practitioner can further determine an actual intermediate tooth configuration that can redirect the treatment. Subsequently, the practitioner determines the configurations that follow the newly determined actual intermediate arrangement for producing additional appliances for the re-directed treatment. In particular, once the practitioner decides that an initially determined set of treatment steps and appliances is not adequate, the practitioner can determine the actual intermediate tooth configuration that has been achieved, either by taking a mold or by direct scanning of the teeth, e.g. as described in U.S. Pat. No. 5,975,893, previously incorporated herein by reference. Once the intermediate configuration is known, subsequent successive movement steps can be calculated and appropriate positioning appliances planned, also as described in U.S. Pat. No. 5,975,893. A new set of appliances can then be produced and treatment resumed. In some cases, it might be appropriate to only partially plan the treatment at the outset with the intention of making a second (and perhaps third, fourth, or more) at a time after the outset of treatment. The manipulable and reconfigurable dental model systems may optionally be used with the appliance planning protocols that rely on determining one or more actual intermediate tooth configurations during the course of a single treatment. The treatment cycle of observation of the intermediate configurations followed by either continuation to the successive configuration or modification of the treatment configuration can be repeated until the practitioner is satisfied that the final tooth arrangement has been achieved, at which time the treatment may end.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An improved method for treating a patient with the use of appliances having cavities shaped to receive and resiliently reposition teeth, wherein the improvement comprises:

producing at the outset of treatment a number of successive appliances which when worn successively by a patient move teeth and/or dental features through desired intermediate arrangements and to a final desired arrangement;

determining that the patient's teeth and/or dental features have moved to an actual arrangement wherein at least one of the successive appliances produced at the outset of treatment is unable to move the teeth and/or dental features to its successive desired intermediate arrangement or the final desired arrangement; and producing at least one additional appliance at a later time having a configuration to move the teeth and/or dental features from the actual arrangement to a new intermediate arrangement wherein at least one of the successive appliances produced at the outset of treatment is able to move the teeth and/or dental features from the new intermediate arrangement to one of said desired intermediate or final desired arrangements.

2. An improved method as in claim 1, wherein the number of appliances produced at the outset of treatment comprises at least three appliances.

3. An improved method as in claim 1, further comprising generating a model of the actual intermediate arrangement prior to the producing of the at least one additional appliance at a later time.

4. An improved method as in claim 3, wherein generating the model comprises taking a mold of the patient's teeth after the determining step.

5. An improved method as in claim 1, wherein at least some of the appliances comprise polymeric shells.

6. An imposed method as in claim 5, wherein at least some of the polymeric shells are thin polymeric shells.

* * * * *